(12) United States Patent
Yi

(10) Patent No.: US 10,869,772 B2
(45) Date of Patent: Dec. 22, 2020

(54) ELECTRONIC ARTIFICIAL HAND

(71) Applicant: MAND.RO CO.,LTD., Seoul (KR)

(72) Inventor: Sang Ho Yi, Seoul (KR)

(73) Assignee: MAND.RO CO., LTD., Seoul (KR)

( * ) Notice: Subject to any disclaimer, the term of this patent is extended or adjusted under 35 U.S.C. 154(b) by 223 days.

(21) Appl. No.: 16/021,481

(22) Filed: Jun. 28, 2018

(65) Prior Publication Data

US 2018/0303633 A1 Oct. 25, 2018

Related U.S. Application Data

(63) Continuation of application No. PCT/KR2015/014554, filed on Dec. 31, 2015.

(30) Foreign Application Priority Data

Dec. 31, 2015 (KR) .......................... 10-2015-0190811

(51) Int. Cl.
| | | |
|---|---|---|
| A61F 2/54 | (2006.01) | |
| A61F 2/58 | (2006.01) | |
| A61F 2/70 | (2006.01) | |
| A61F 2/72 | (2006.01) | |
| A61F 2/68 | (2006.01) | |
| B25J 15/00 | (2006.01) | |

(52) U.S. Cl.
CPC ................ *A61F 2/583* (2013.01); *A61F 2/58* (2013.01); *A61F 2/70* (2013.01); *A61F 2/72* (2013.01); *A61F 2002/6872* (2013.01); *A61F 2002/701* (2013.01); *B25J 15/0023* (2013.01)

(58) Field of Classification Search
CPC ............... A61F 2/54; A61F 2/58; A61F 2/583
See application file for complete search history.

(56) References Cited

U.S. PATENT DOCUMENTS

| | | | | |
|---|---|---|---|---|
| 4,986,723 A | * | 1/1991 | Maeda | ....................... B25J 9/06 294/111 |
| 5,200,679 A | * | 4/1993 | Graham | ............... B25J 15/0009 294/111 |
| 9,016,744 B2 | * | 4/2015 | Starkey | ................... A61F 2/583 294/111 |
| 9,314,932 B2 | * | 4/2016 | Ciocarlie | ................. B25J 15/08 |
| 10,426,636 B2 | * | 10/2019 | Mandl | ..................... A61F 2/586 |
| 2018/0280164 A1 | * | 10/2018 | Sikdar | ................... A61B 8/085 |

* cited by examiner

*Primary Examiner* — Bruce E Snow
(74) *Attorney, Agent, or Firm* — Novick, Kim & Lee, PLLC; Jae Youn Kim

(57) ABSTRACT

The present invention relates to an electronic artificial hand including a power section, a tendon section, and a restoring line section for joint movement of a finger group which is capable of preventing unnecessary driving of the power section using tension of the tendon section caused by the joint movement of the finger group and implementing a gripping force similar to a gripping force of a person through a physical configuration using the tension of a spring section and the tendon section and which is easily implemented due to a simplified configuration and has low manufacturing costs.

9 Claims, 16 Drawing Sheets

ELECTRONIC ARTIFICIAL HAND

CROSS-REFERENCE TO RELATED APPLICATION

This application is a Continuation of International Patent Application No. PCT/KR2015/014554 filed Dec. 31, 2015, and claims priority to and the benefit of Korean Patent Application No. 10-2015-0190811, filed on Dec. 31, 2015, the disclosure of which is incorporated herein by reference in its entirety.

TECHNICAL FIELD

The present invention relates to an electronic artificial hand. More particularly, the present invention relates to an electronic artificial hand which provides a predetermined gripping force, controls unnecessary driving to minimize power loss, and is easily implemented at an inexpensive cost.

BACKGROUND ART

An electronic artificial hand configured to replace a hand, a leg, or the like of a disabled patient implements joint movement using a motor or implements joint movement using a string or the like according to a sort. When the joint movement is implemented using the motor, since the motor is provided in each joint, substantial power is required, and since a weight of the electronic artificial hand is heavy, the electronic artificial hand becomes a burden on the strength of a wearer. Particularly, since each joint is implemented by the motor and controlled by software, manufacturing cost increases and maintenance, repair, and management are not easy. In the case of the electronic artificial hand configured to implement the joint movement using the string, or the like, although manufacturing costs are cheaper than that of the electronic artificial hand using only the motor, individually controlling each finger is difficult, and since each joint is not individually driven but integrally driven, a gripping force for gripping a target object cannot be easily implemented, and thus stability is inferior. Particularly, the electronic artificial hand cannot implement a predetermined gripping force like a human hand after gripping the target object. To solve the problem, the predetermined gripping force can be implemented through additional joint movement equal to a predetermined power after sensing joint movement limit value by storing a predetermined power value in the motor or the like in advance. However, the sensor and the previously stored predetermined power value should be requisitely input in advance, and the gripping force cannot be variously implemented according to conditions or the target object.

Korean Utility Model Registration No. 20-0238152 (prior document) relates to an artificial functional hand, and provides an artificial hand configured to implement various joints like joints of a human. However, in a case of the prior document, since all fingers perform joint movement through one power section, when gripping a target object, the target object cannot be delicately gripped, and stability is inferior. Particularly, as an example, when gripping the target object having different edge surfaces, since edges gripped by the fingers are different but all the fingers perform joint movement through one power section, the different edges are not sensed and the target object is incompletely gripped. Further, since the prior document does not have a configuration capable of implementing a predetermined gripping force while gripping a target, and thus the joint movement is stopped when the fingers comes into contact with an edge surface of the target, the target object cannot be firmly gripped. Further, since a configuration configured to stop the power section at a joint movement limit is not separately provided, power loss occurs due to unnecessary operations, and accordingly, probability of occurrence for an error or a failure increases, and maintenance, repair, and management are not easy.

DISCLOSURE

Technical Problem

The present invention is directed to providing an electronic artificial hand which is easily implemented.

Further, the present invention is directed to providing an electronic artificial hand of which each finger is individually driven.

Meanwhile, the present invention is directed to providing an electronic artificial hand of which each finger does not perform joint movement excessively in one direction or the other direction.

Further, the present invention is directed to providing an electronic artificial hand configured to minimize an unnecessary operation or use of power.

In addition, the present invention is directed to providing an electronic artificial hand configured to minimize loss of power due to wasted power.

In addition, the present invention is directed to providing an electronic artificial hand configured to implement a predetermined gripping force to firmly grip a target object.

Technical Solution

One aspect of the present invention provides an electronic artificial hand including a gripping part including a plurality of finger groups each having a power section and a controller configured to operate the power section, wherein the power section perform joint movement of the gripping part in one direction to perform a gripping operation or performs joint movement of the gripping part in the other direction to perform an unfolding operation.

Advantageous Effects

According to the present invention, since each of the finger groups includes a power section and a switch part configured to stop the power section, a target object can be firmly gripped, and further, a target object having different edges can be stably gripped.

Further, according to the present invention, since the power section is stopped by a first switch part in order to prevent excessive joint movement in the other direction in which the finger groups are unfolded, power loss can be prevented, and since damage can be prevented, maintenance, repair, and management are easy.

Meanwhile, according to the present invention, the first switch part uses tension of a tendon section to stop the power section, and thus implementation can be easy, and a first switch is physically stopped by the tendon section and thus maintenance, repair, and management are easy.

Further, according to the present invention, since the power section is stopped by a second switch part in order to prevent excessive joint movement in one direction in which the finger groups grip, power loss can be prevented, and since damage can be prevented, maintenance, repair, and management are easy.

In addition, according to the present invention, since the second switch part uses the tension of the tendon section to stop the power section and thus implementation is easy, the first switch is physically stopped by the tendon section and thus the maintenance, the repair, and the management are easy.

In addition, since a support member presses the second switch part when tension which is greater than a restoring force of a spring section is generated, a predetermined gripping force corresponding to the restoring force of the spring section can be implemented, and the target object can be more firmly gripped.

BEST MODE

Figure 1:
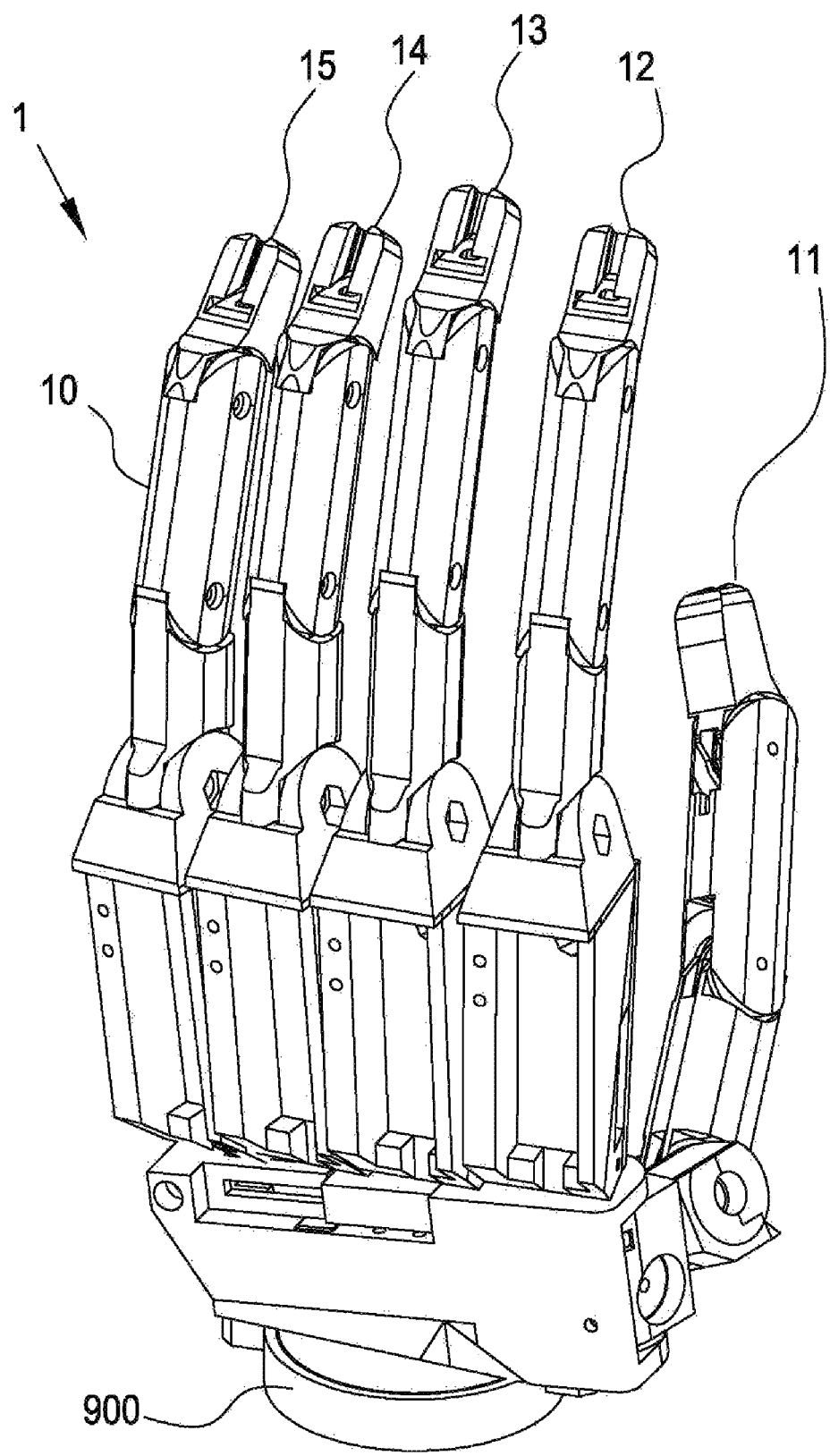
FIG. 1 is a view illustrating a gripping part of an electronic artificial hand according to an embodiment of the present invention.

According to an aspect of the present invention, an electronic artificial hand includes a wearing part worn on an impaired area, a gripping part engaged with the wearing part and including a plurality of finger groups, and a controller provided in the wearing part or the gripping part to control a power section, wherein the finger groups, each including the power section, perform joint movement in one direction through the power section to grip or perform joint movement in the other direction to perform an unfolding operation. Further, the finger groups each include: a body part including the power section; a first knuckle, a second knuckle, and a third knuckle sequentially engaged with one end of the body part; a joint part configured to sequentially engage the body part, the first knuckle, the second knuckle, and the third knuckle and perform joint movement on the body part, the first knuckle, the second knuckle, and the third knuckle in one direction to a predetermined angle; a tendon section having one end connected to the power section to be wound and the other end configured to sequentially pass through the body part, the first knuckle, the second knuckle, and the third knuckle to be connected to third knuckle; a tendon path formed in each of the body part, the first knuckle, the second knuckle, and the third knuckle and through which the tendon section passes; a restoring line section having one end connected to the body part and the other end sequentially passing through the body part, the first knuckle, the second knuckle, and the third knuckle to be connected to the third knuckle, and having a predetermined restoring force; and a restoring line path formed in each of the body part, the first knuckle, the second knuckle, and the third knuckle, and through which the restoring line section passes. The tendon path is formed to be eccentric in the one direction on the basis of the joint part, the restoring line path is formed to be eccentric in the other direction on the basis of the joint part, the body part includes a first switch part at a location close to the tendon section, the first switch part is pressed by tension of the tendon section generated by the predetermined restoring force of the restoring line section, the tendon section has a length greater than that of the tendon path and thus the tension is removed due to unwinding of the power section, the first switch part is decompressed to stop the power section when the tension is removed, and the body part further includes a support member configured to reverse a proceeding direction of the tendon section because the tendon section is hooked on the body part, a guide groove formed along a direction in which the tension of the tendon section is generated, and with which the support member is engaged to move, a second switch part provided in one end of the guide groove and pressed by movement of the support member, and a spring section having one end connected to the support member, and the other end connected to the other end of the guide groove.

Modes of the Invention

Hereinafter, exemplary embodiments of the present invention will be described in detail with reference to the accompanying drawings which may allow one of ordinary skill in the art to easily perform the present invention. However, the present invention may be implemented in various forms and is not limited to the embodiments which will be described below. Components not related to the description are omitted in the drawings to clearly disclose the present invention, and the same reference symbols in the drawings refer to the same or similar components.

Purposes and effects of the present invention may be naturally understood or may become apparent due to descriptions which will be described below, but are not limited by the following descriptions which will be described below.

Purposes, characteristics, and advantages of the present invention may be more apparent through the following specific descriptions. Further, when the detailed description of the disclosed art related to the present invention is determined to unnecessarily obscure the spirit of the present invention, the detailed description will be omitted. Hereinafter, embodiments of the present invention will be described in detail with reference to the accompanying drawings.

Referring to FIGS. 1 to 4, an electronic artificial hand according to an embodiment of the present invention includes a wearing part 2 worn on an impaired area, a gripping part 1 engaged with the wearing part 2 and capable of gripping a target object 4, and a controller 3 configured to control the gripping part 1. Here, the gripping part 1 may include a plurality of finger groups 10. Further, the finger groups 10 each include a power section 400 and are individually driven. In detail, the finger groups 10 may perform joint movement in one direction (a) through the power section 400 to grip, or perform joint movement in the other direction (b) to perform an unfolding operation. In more detail, when the power section 400 is operated and the finger groups 10 winds (a') a tendon section 500, the finger groups 10 may perform joint movement in the one direction (a) to grip the target object 4, and when the power section 400 is operated and the tendon section 500 is unwound (b'), the finger groups 10 may perform joint movement in the other direction (b) to release the gripped target object 4.

Figure 3:
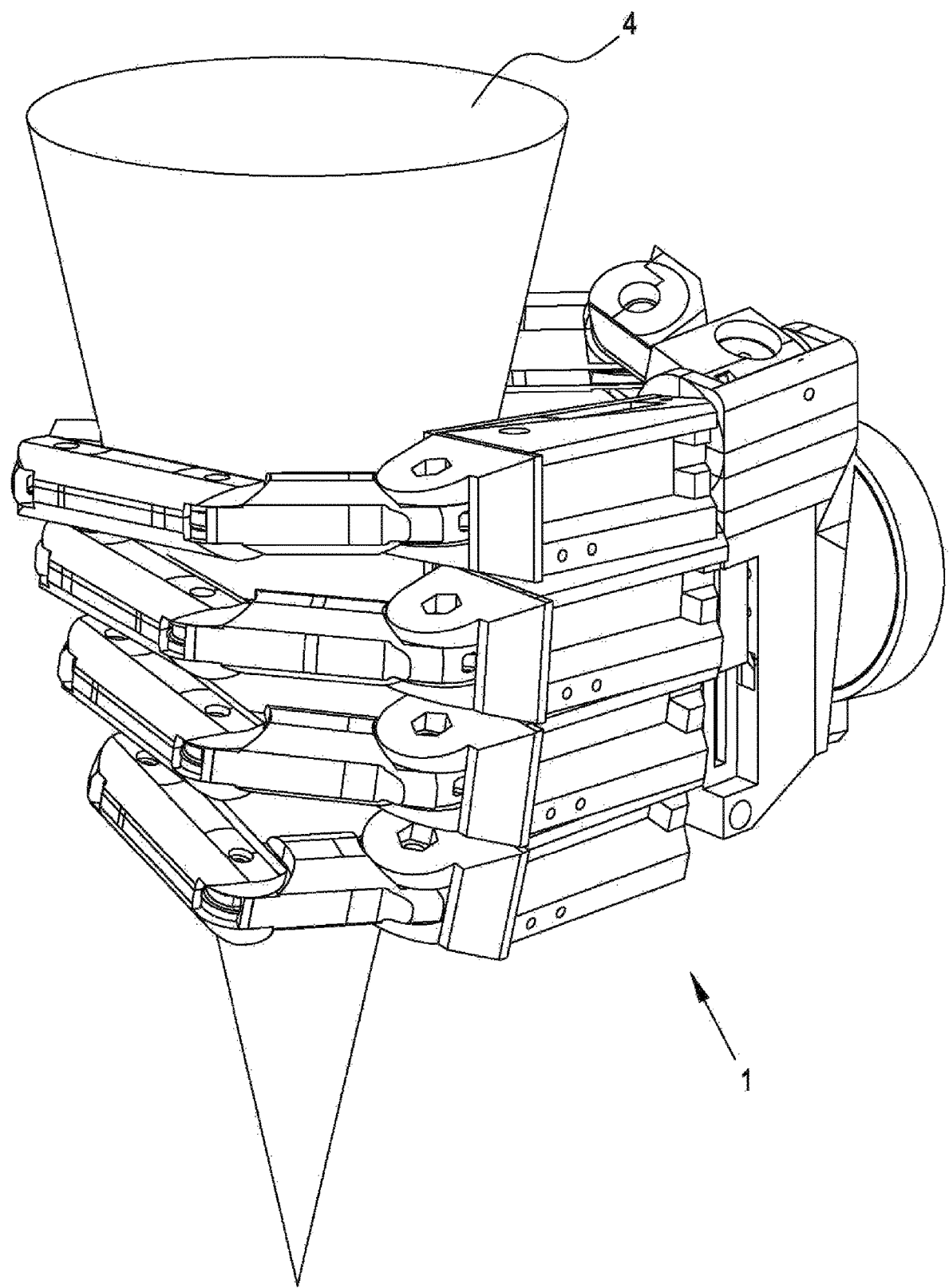
FIG. 3 is a view illustrating that the gripping part of the electronic artificial hand according to the embodiment of the present invention grips a target object having different edges.
Figure 4:
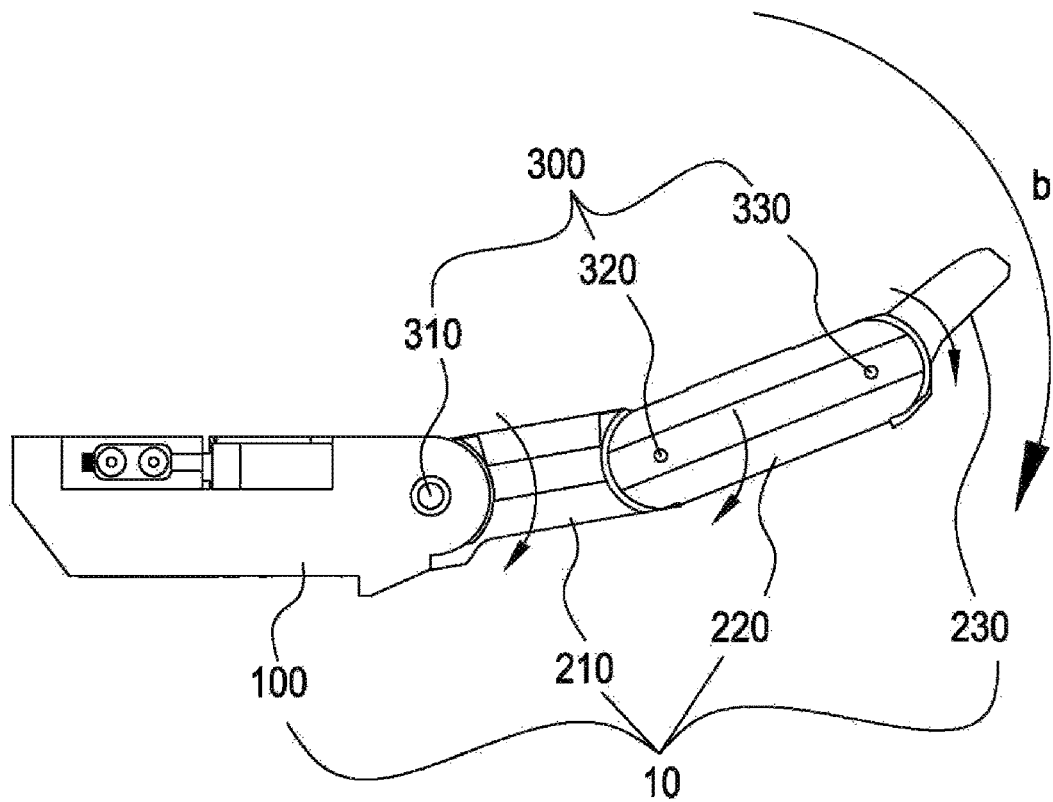
FIG. 4 is a view illustrating that the finger groups of the electronic artificial hand according to the embodiment of the present invention perform joint movement in one direction and the other direction.
Figure 4:
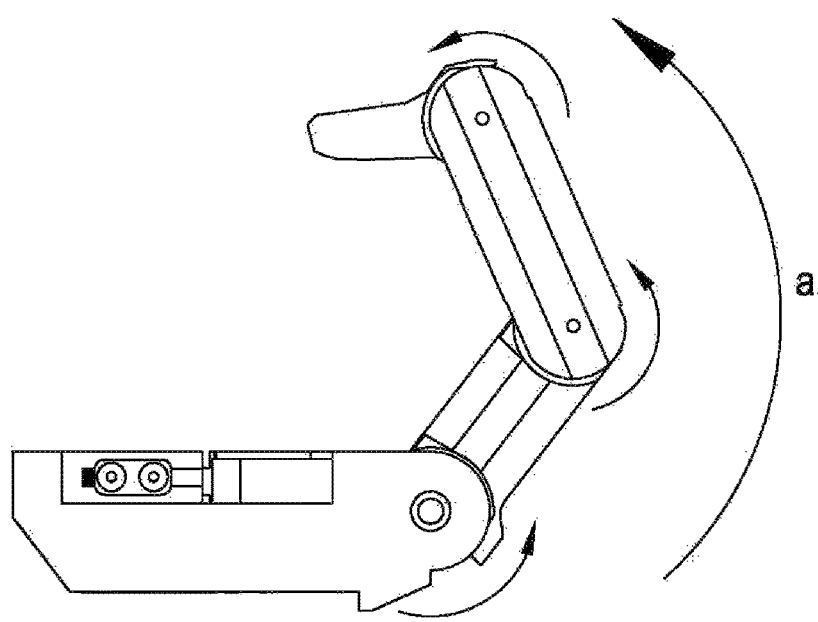

Referring to FIG. 3, the gripping part 1 includes the plurality of finger groups 10, and each of the finger groups 10 may be individually operated by including the power section 400. Further, the finger groups 10 are individually driven and thus may be continuously used even when damage or a malfunction of one finger occurs. Further, since the finger groups 10 are individually operated, a relatively greater gripping force may be implemented. Specifically, the finger groups 10 may be individually operated, and thus more stably grip the target object 4 having various shapes or forms. More specifically, when a plurality of fingers are driven using one power section 400, and the target object 4 has an upper edge and a lower edge different from each other, since a part having a large edge is gripped by one finger group and stopped and then the remaining finger groups 10 stops without gripping a part having a small edge, the target object 4 is not evenly gripped and thus stability is reduced. However, when the finger groups 10 are driven by each including the power section 400 like the present invention, since the finger group 10 griping a large edge surface stops but the remaining finger groups 10 perform joint movement to a gripping limit, the target object 4 may be stably and firmly gripped.

Figure 2:
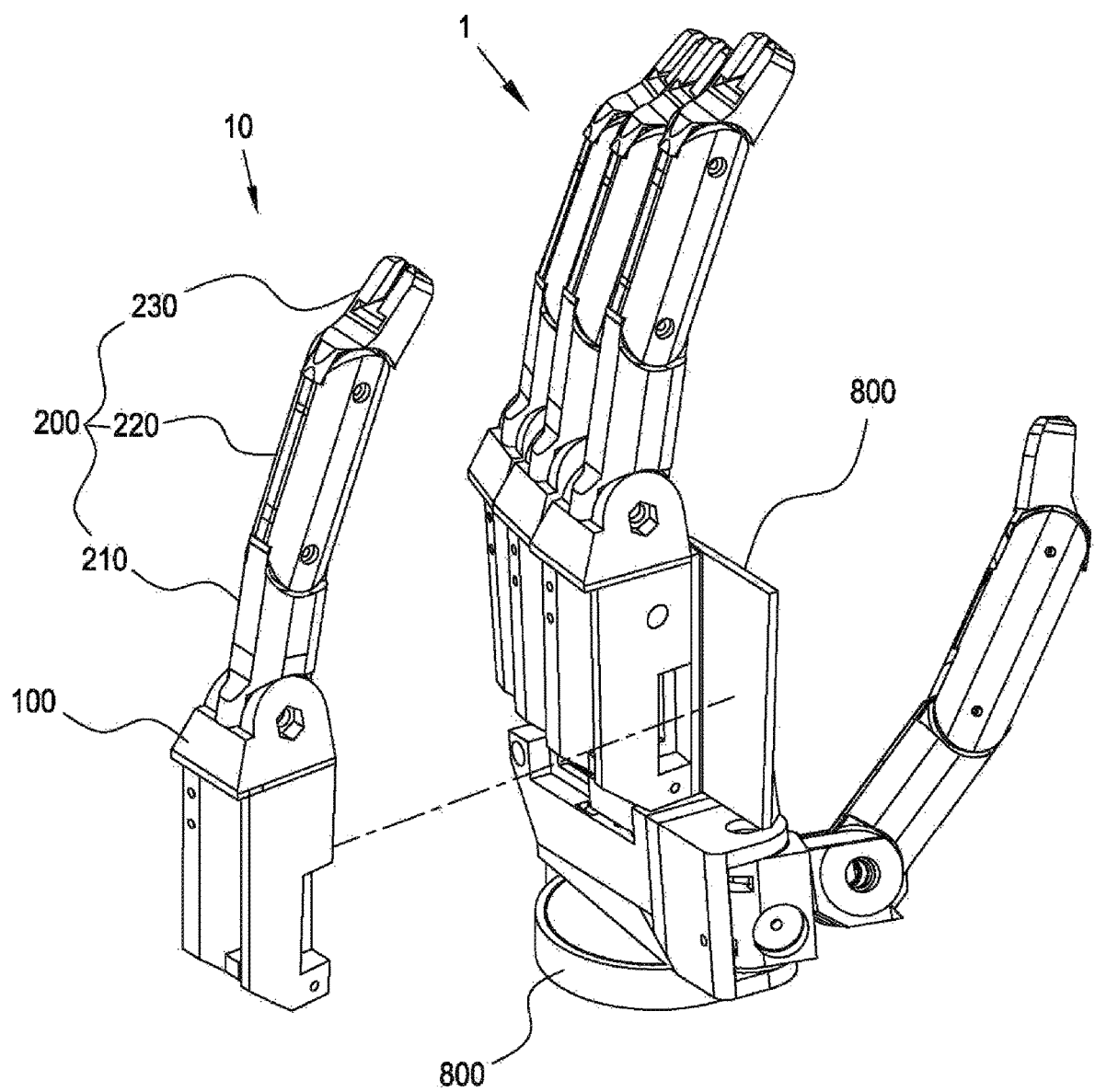
FIG. 2 is a view illustrating finger groups of the electronic artificial hand according to the embodiment of the present invention.

Referring to FIGS. 1 and 2, the gripping part 1 may include five finger groups 10. Further, one finger group 10 among the five finger groups 10 may be a thumb group 11. The thumb group 11 may be provided at an angle different from those of the remaining four finger groups 10 excluding the thumb group 11, and the thumb group 11 may be provided at the angle different from those of the remaining finger groups 10 so as to be disposed to have an end configured to come into contact with ends of the remaining finger groups 10. That is, since the end of the thumb group 11 among the five finger groups 10 is disposed to come into contact with the ends of the remaining four finger groups 10, the target object 4 can be gripped. Specifically, since the thumb group 11 grips the target object 4 at a different angle, the target object 4 may be stably and firmly gripped. Meanwhile, the five finger groups 10 may include the thumb group 11, an index finger group 12, a middle finger group, a ring finger group 14, and a little finger group 15, and may each have a length and a shape corresponding to those of a thumb, an index finger, a middle finger, a ring finger and a little finger. Meanwhile, the thumb group 11 may have a first joint part 310 located between a first knuckle 210, and a body part 100 and formed from double joints. The double joints may change the angle of the thumb group 11 according to a demand of a user, and may be fixed by a magnet or the like to be used.

Referring to FIGS. 4 to 7, each of the finger groups 10 may include the power section 400, the body part 100 including the power section 400, a knuckle part 200 including the first knuckle 210, a second knuckle 220, and a third knuckle 230 sequentially engaged with one end of the body part 100, a joint part 300 configured to engage each of the body part 100, the first knuckle 210, the second knuckle 220 and the third knuckle 230, the tendon section 500 configured to perform joint movement of each knuckle in the one direction (a), a tendon path 501 through which the tendon section 500 passes, a restoring line section 550 to perform joint movement of each knuckle in the other direction (b), and a restoring line path 551 through which the restoring line section 550 passes.

Figure 5:
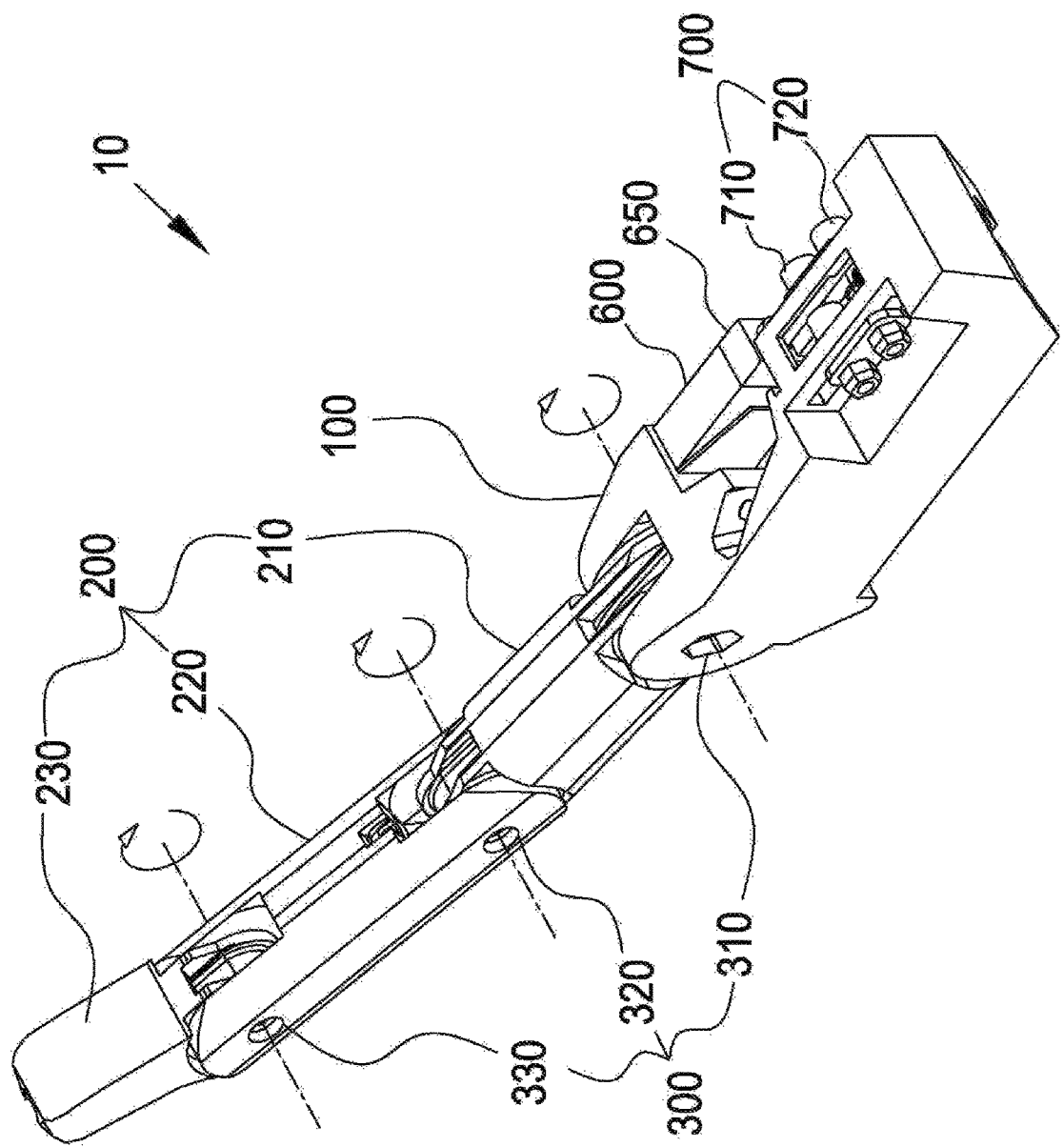
FIG. 5 is a view illustrating the finger group of the electronic artificial hand according to the embodiment of the present invention.
Figure 6:
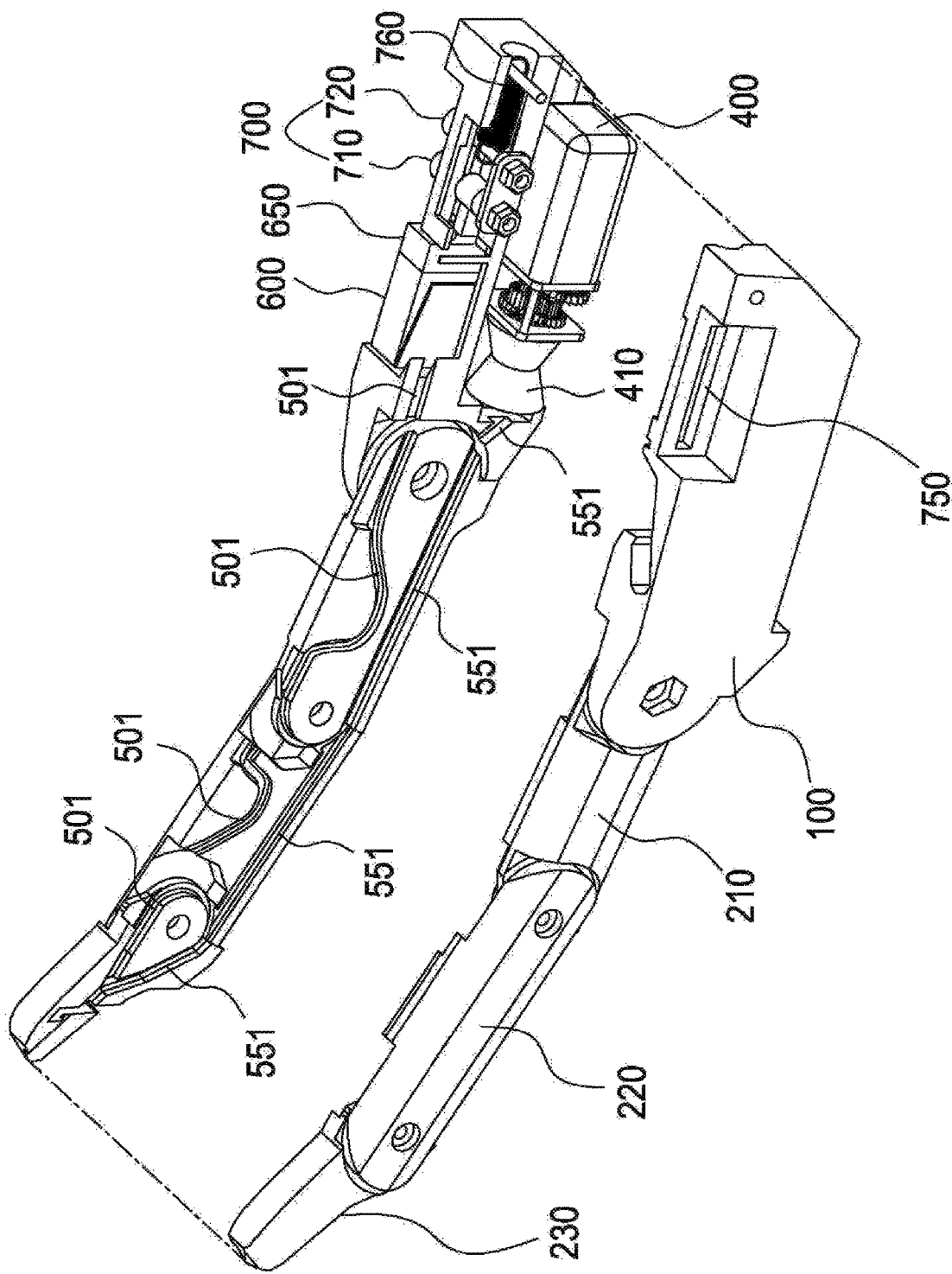
FIG. 6 is a cut-away view illustrating the finger group of the electronic artificial hand according to the embodiment of the present invention.
Figure 7:
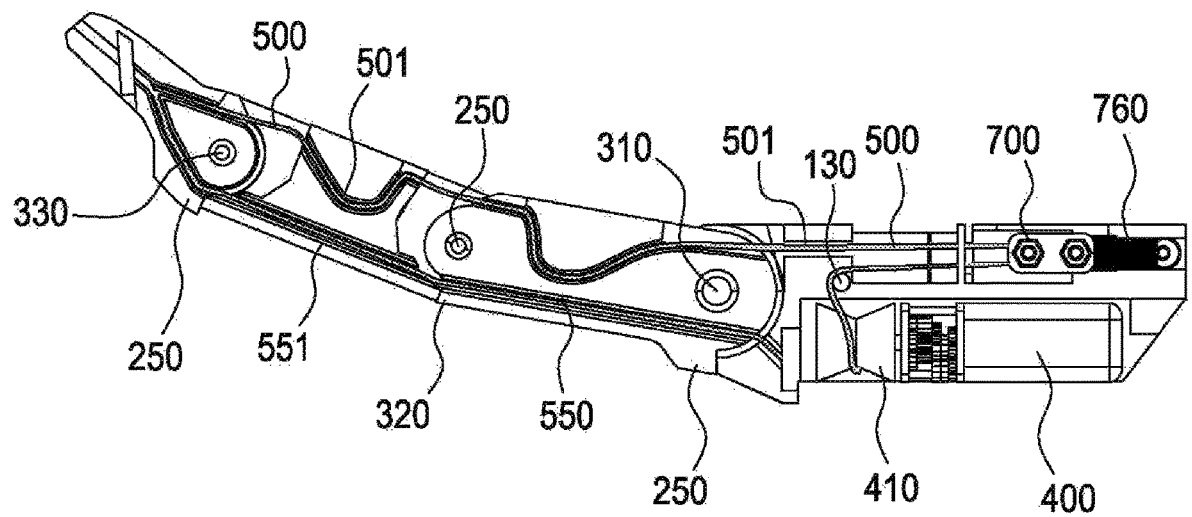
FIG. 7 is a cross-sectional view illustrating the joint movement of the finger groups of the electronic artificial hand according to the embodiment of the present invention.
Figure 7:
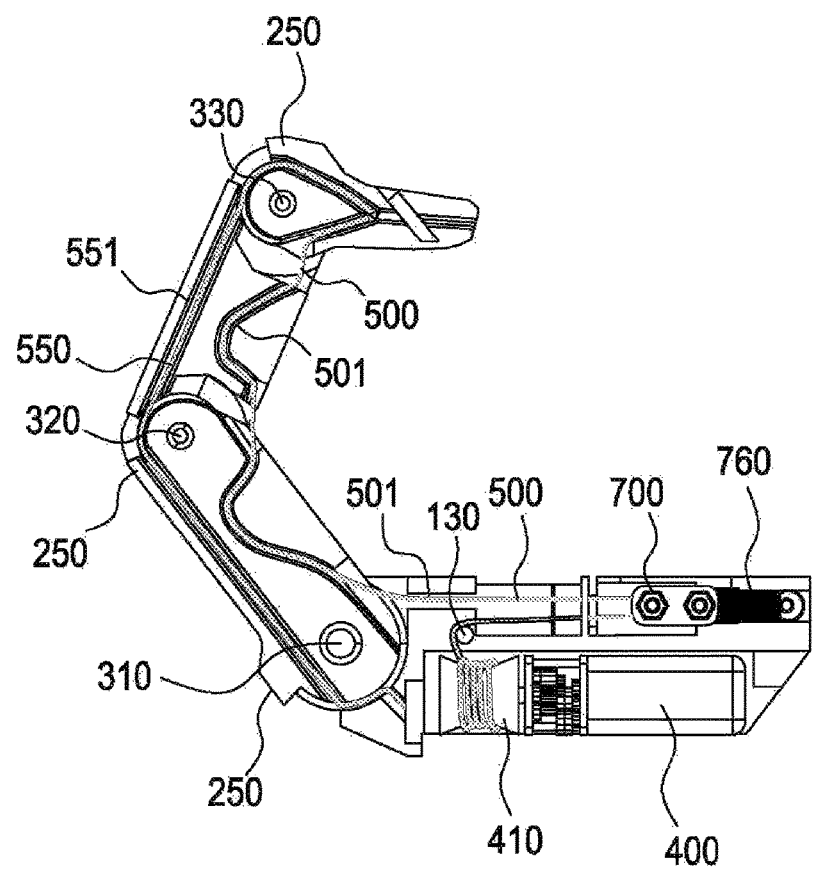

Referring to FIG. 2, five finger groups 10 may be disposed as one set to have a human hand shape. Here, five body parts 100 are engaged to form a palm shape. Accordingly, the body part 100 may have a location, a size, and a shape corresponding to those of a metacarpal bone. Referring to FIGS. 5 to 7, the body part 100 includes the power section 400. The power section 400 may be a motor. In detail, the power section 400 may include a motor including a plurality of gears. In more detail, the power section 400 may include the plurality of gears having various gear ratios to be a motor having relatively greater stability. The tendon section 500 is connected to the power section 400 to be wound (a'). A winding part 410 in a reel shape and having a groove formed so that the tendon section 500 may be easily wound (a') or unwound (b') may be engaged with the power section 400 to perform rotational movement with the power section 400. Here, winding (a') refers to being rolled to be wound, and unwinding (b') refers to being unfolded from a wound state.

The body part 100 includes the knuckle part 200 on the one end thereof. The knuckle part 200 includes the first knuckle 210, the second knuckle 220, and the third knuckle 230 sequentially engaged with the one end of the body part 100. Here, the first knuckle 210, the second knuckle 220, and the third knuckle 230 are configurations corresponding to knuckles of each finger. Specifically, the first knuckle 210 may correspond to a hand knuckle bone, the second knuckle 220 may correspond to a middle knuckle bone, and the third knuckle 230 corresponds to an end knuckle bone. Each of the body part 100, the first knuckle 210, the second knuckle 220, and the third knuckle 230 are engaged through the joint part 300. The joint part 300 may perform joint (rotation) movement to a predetermined angle on each of the first knuckle 210, the second knuckle 220, and the third knuckle 230. In detail, the joint part 300 may connect the first knuckle 210, the second knuckle 220, and the third knuckle 230, and the joint part 300 may perform joint movement to a predetermined angle on each of the first knuckle 210, the second knuckle 220, and the third knuckle 230 in the one direction (a). In more detail, the joint part 300 may include the first joint part 310 configured to engage the body part 100 and the first knuckle 210, a second joint part 320 configured to connect the first knuckle 210 and the second knuckle 220, and a third joint part 330 configured to connect the second knuckle 220 and the third knuckle 230. Specifically, to describe the first knuckle 210 and the second knuckle 220 as an example, the first knuckle 210 and the second knuckle 220 may each be provided as a female and a male to be coupled to each other and may be engaged with each other through a bolt, a pin, a hinge, and the like to perform joint movement. Further, the joint part 300 may have a protrusion 250 formed at one side thereof to perform joint movement within a limited predetermined angle like the human hand. In detail, the protrusion 250 configured to physically prevent the joint movement of the first knuckle 210, the second knuckle 220, and the third knuckle 230 may be formed so that the first knuckle 210, the second knuckle 220, and the third knuckle 230 may be prevented from excessively performing joint movement in the other direction (b) beyond a virtual extension line of the one end of the body part 100 when performing joint movement. Accordingly, the first knuckle 210, the second knuckle 220, and the third knuckle 230 perform joint (rotational) movement in both the one direction (a) and the other direction (b), but, due to the protrusion 250, do not perform joint movement beyond the virtual extension line of the one end of the body part 100 when performing joint movement in the other direction (b). Here, the virtual extension line of the one end of the body part 100 refers to an extension line in which the body part 100, the first knuckle 210, the second knuckle 220, and the third knuckle 230 are serially located. However, scope of the joint movement is not limited within the virtual extension line, and the first knuckle 210, the second knuckle 220, and the third knuckle 230 may be used by adjusting and changing a location of the protrusion 250 depending on a manufacturer or a user.

Referring to FIGS. 6 and 7, the tendon section 500 may have one end connected to the power section 400 to be wound (a') or unwound (b'). The tendon section 500 is wound (a') or unwound (b') through rotational movement of the power section 400 to perform joint movement of the finger groups 10. In detail, since the one end of the tendon section 500 is connected to the power section 400, the tendon section 500 is wound (a') to perform joint movement of the finger groups 10 in the one direction (a), and unwound (b') to perform joint movement of the finger groups 10 in the other direction (b). The tendon section 500 has the one end connected to the power section 400, and the other end sequentially passing through the body part 100, the first knuckle 210, the second knuckle 220, and the third knuckle 230 to be connected to the third knuckle 230. In detail, each of the body part 100, the first knuckle 210, the second knuckle 220, and the third knuckle 230 has the tendon path 501, through which the tendon section 500 passes, and since the tendon section 500 passes through the tendon path 501, the one end and the other end of the tendon section 500 are each connected to the power section 400 and the third knuckle 230. In more detail, the tendon path 501 and the tendon section 500 are formed to be eccentric in the one direction (a) in which the finger groups 10 perform joint movement and grip on the basis of the joint part 300. In more detail, the tendon path 501 and the tendon section 500 are formed to be eccentric in the one direction (a) in which the finger groups 10 perform joint movement on the basis of the first joint part 310, the second joint part 320 and the third joint part 330. Accordingly, since the tendon section 500 and the tendon path 501 are formed at a location eccentric in the one direction (a) on the basis of the joint part 300, when the power section 400 winds (a') the tendon section 500, the first knuckle 210, the second knuckle 220, and the third knuckle 230 perform joint movement in the one direction (a). The restoring line section 550 is a configuration configured to restore the finger groups 10 subjected to joint movement in the one direction (a) by performing joint movement of the finger groups 10 in the other direction (b). The restoring line section 550 has one end connected to the body part 100, and the other end sequentially passing through the body part 100, the first knuckle 210, the second knuckle 220, and the third knuckle 230 to be connected to the third knuckle 230.

The restoring line section 550 has a predetermined restoring force. One restoring line section 550 may be provided to sequentially pass through the body part 100, the first knuckle 210, the second knuckle 220, and the third knuckle 230 to be connected to the third knuckle 230, but the restoring line section 550 may be provided in each of the first joint part 310, the second joint part 320, and the third joint part 330 to restore each joint part 300. In detail, the restoring line path 551 through which the restoring line section 550 passes is formed in each of the body part 100, the first knuckle 210, the second knuckle 220, and the third knuckle 230, and since the restoring line section 550 passes through the restoring line path 551, the one end and the other end of the restoring line path 551 are each connected to the body part 100 and the third knuckle 230. In more detail, the restoring line path 551 and the restoring line section 550 are formed to be eccentric in the other direction (b) in which the finger groups 10 perform joint movement and are unfolded on the basis of the joint part 300. In more detail, the restoring line path 551 and the restoring line section 550 are formed to be eccentric in the other direction (b) in which the finger groups 10 perform joint movement and are unfolded on the basis of the first joint part 310, the second joint part 320 and the third joint part 330. Accordingly, the restoring line path 551 and the restoring line section 550 are formed to be eccentric in the other direction (b) on the basis of the joint part 300, and thus restore by performing joint movement in the other direction (b) on the finger groups 10 subjected to joint movement in the one direction (a) by the tendon section 500. Specifically, the restoring line section 550 has a predetermined restoring force and thus performs joint movement of the first knuckle 210, the second knuckle 220, and the third knuckle 230 in the other direction (b) using the predetermined restoring force. In this case, in order to move finger groups 10 in the other direction (b) using the restoring force of the restoring line section 550, the tendon section 500 wound (a') around the power section 400 should be unwound (b'). Here, eccentricity refers to eccentric disposition to one side on the basis of one starting point.

Referring to FIGS. 11 to 14, the body part 100 further includes at least one switch part configured to stop the power section 400 through tension of the tendon section 500 generated by winding (a') or unwinding (b') of the tendon section 500. In detail, at least one switch part, which is configured to stop the power section 400 using the tension of the tendon section 500 generated by winding (a') or unwinding (b') of the tendon section 500 and the restoring force of the restoring line section 550, may be further provided.

Figure 13:
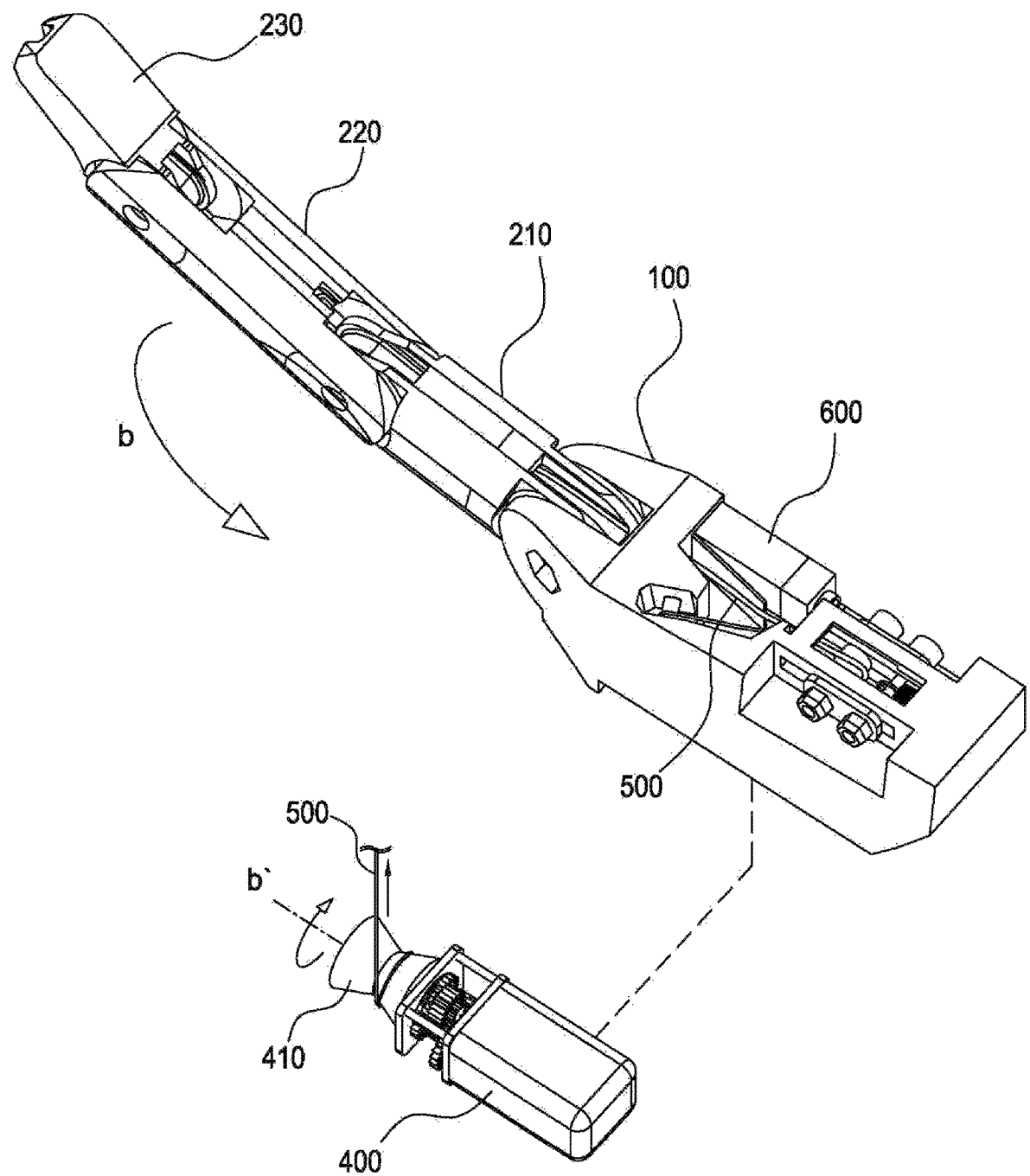
FIG. 13 is a view illustrating that the finger groups of the electronic artificial hand according to the embodiment of the present invention perform joint movement in the other direction.
Figure 14:
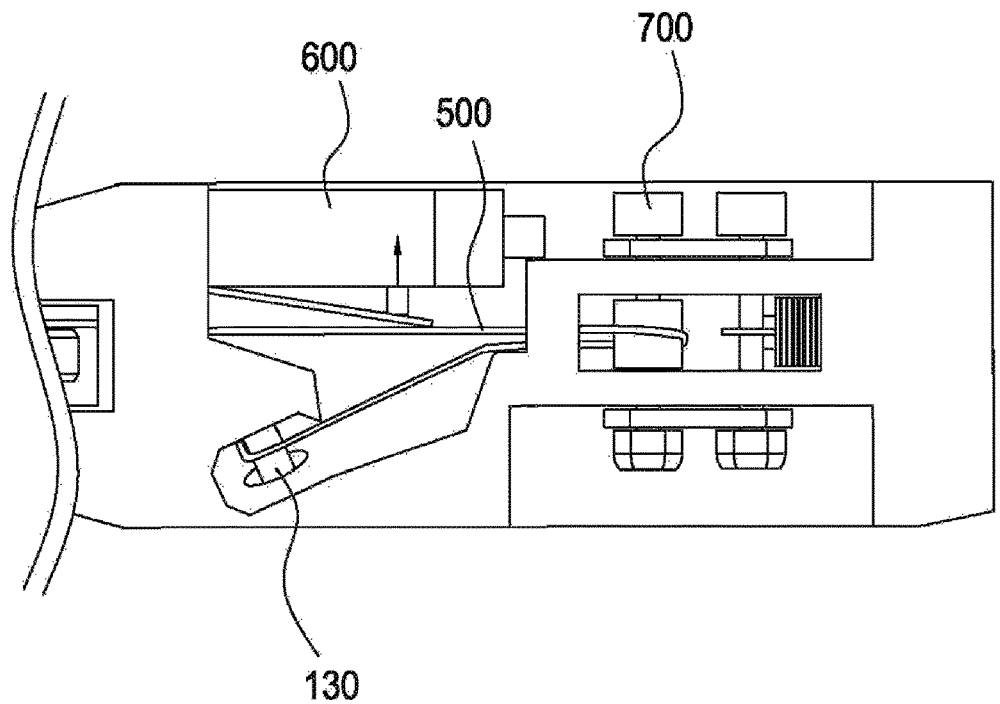
FIG. 14 is a view illustrating an operation of a first switch part of the electronic artificial hand according to the embodiment of the present invention.
Figure 14:
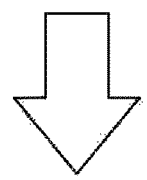
Figure 14:
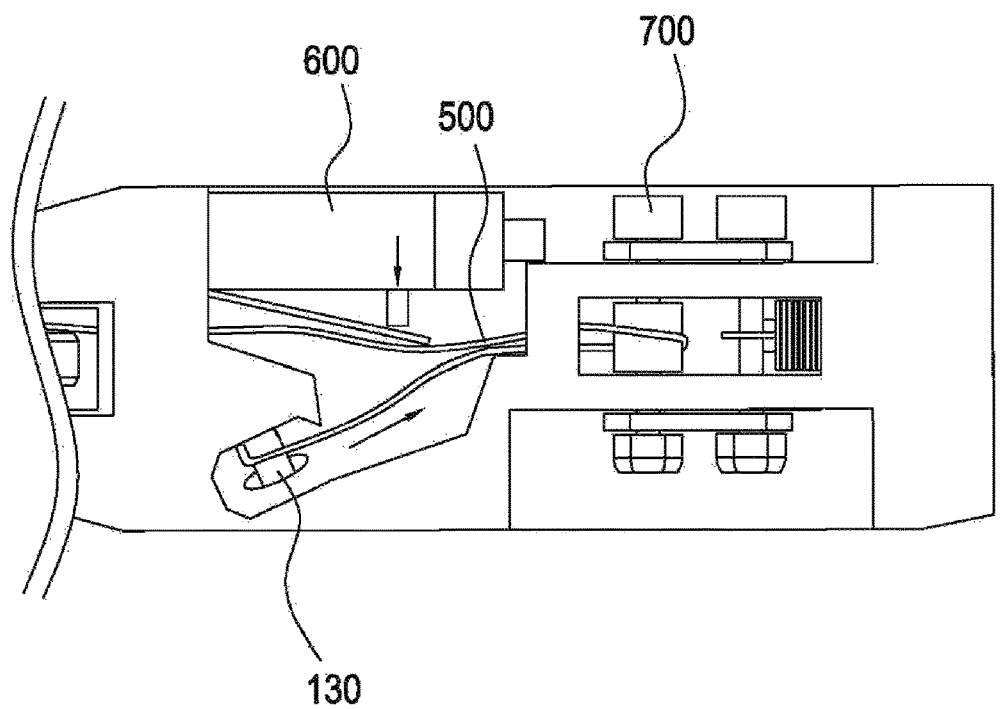

Referring to FIGS. 13 and 14, the body part 100 may include a first switch part 600 capable of stopping excessive joint movement of the finger groups 10 in the other direction (b). The first switch part 600 is provided at a location close to the tendon section 500. The first switch part 600 is provided to be close to the tendon section 500, and when the tension is generated from the tendon section 500 due to winding (a') of the tendon section 500 by the power section 400, and the predetermined restoring force of the restoring line section 550, the first switch part 600 is pressed. Further, when the power section 400 is unwound (b') and then the tension of the tendon section 500 is removed, the first switch part 600 is decompressed. Since the tension of the tendon section 500 is removed, the first switch part 600 stops the power section 400 when being decompressed. The first switch part 600 stops the power section 400 physically or through electric signals. Specifically, the tension is generated from the tendon section 500 due to winding (a') of the power section 400 and the predetermined restoring force of the restoring line section 550. When the power section 400 is unwound (b'), and the finger groups 10 perform joint movement in the other direction (b) to move to maximum joint scope at which the protrusion 250 is formed, the restoring force of the restoring line section 550 is removed, and in this case, since the power section 400 is unwound (b'), the tension of the tendon section 500 is removed. Accordingly, the tendon section 500 is formed to be longer than the tendon path 501. In detail, the tendon section 500 is provided to be longer than the tendon path 501, and a basic length of the tendon path 501 refers to a length of the tendon path 501 when each of the finger groups 10 performs joint movement to have the longest length. Specifically, the length of the tendon path 501 refers to a maximum distance from the power section 400, to which the tendon section 500 is connected to, to the third knuckle 230 when the finger groups 10 perform joint movement in the other direction (b) maximally. That is, the length of the tendon path 501 refers to a length when the finger groups 10 are moved to maximum joint movement scope in the other direction (b) and stopped by the protrusion 250. When the tendon section 500 is provided to have a length greater than that of the tendon path 501, since the tendon section 500 of the power section 400 is unwound (b') to be longer than the tendon path 501 while being unwound (b'), the tension of the tendon section 500 is removed. Meanwhile, the first switch part 600 may include a button type switch. As an example, the first switch part 600 may include a limit switch.

Figure 11:
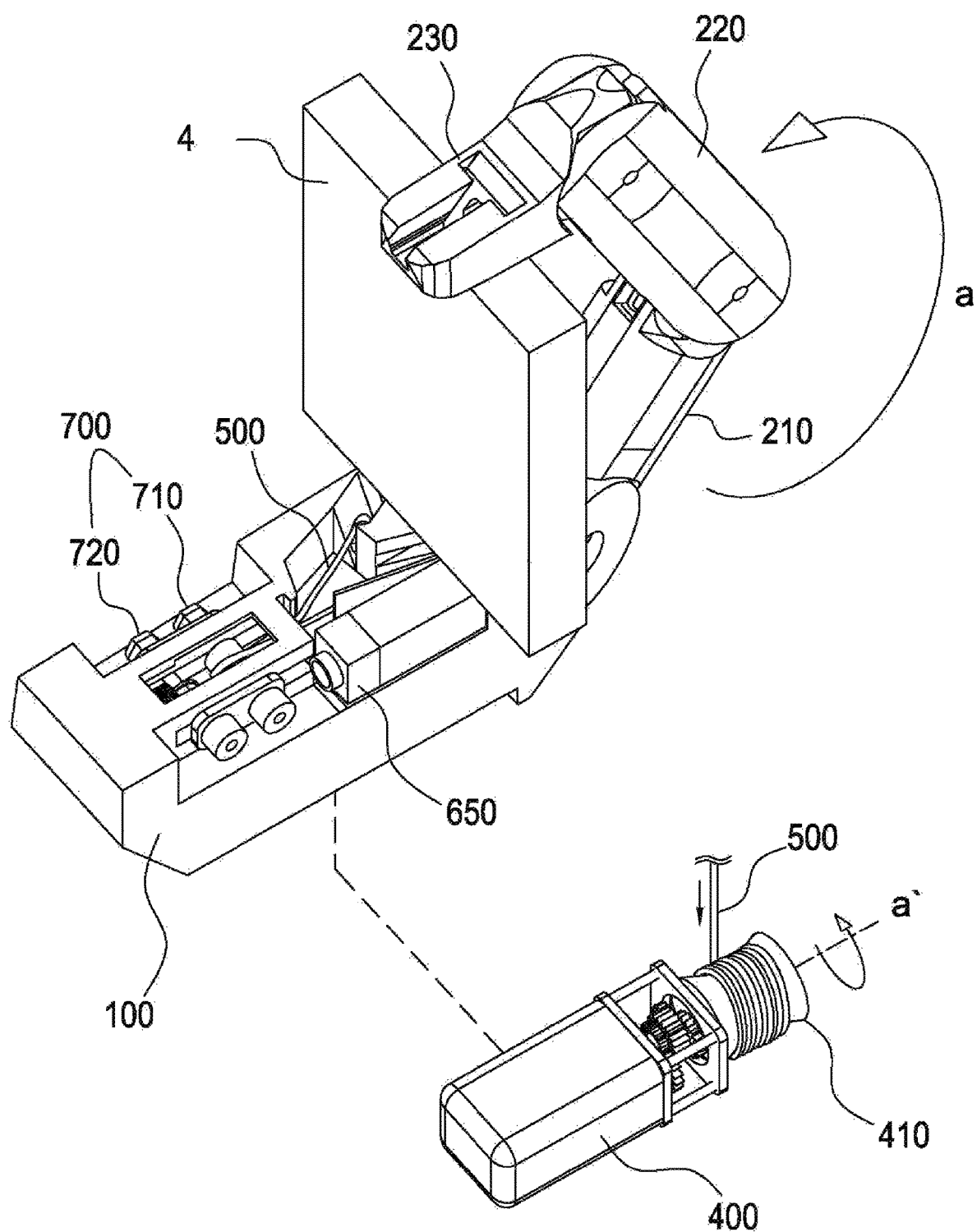
FIG. 11 is a view illustrating that the finger groups of the electronic artificial hand according to the embodiment of the present invention perform joint movement in the one direction.
Figure 12:
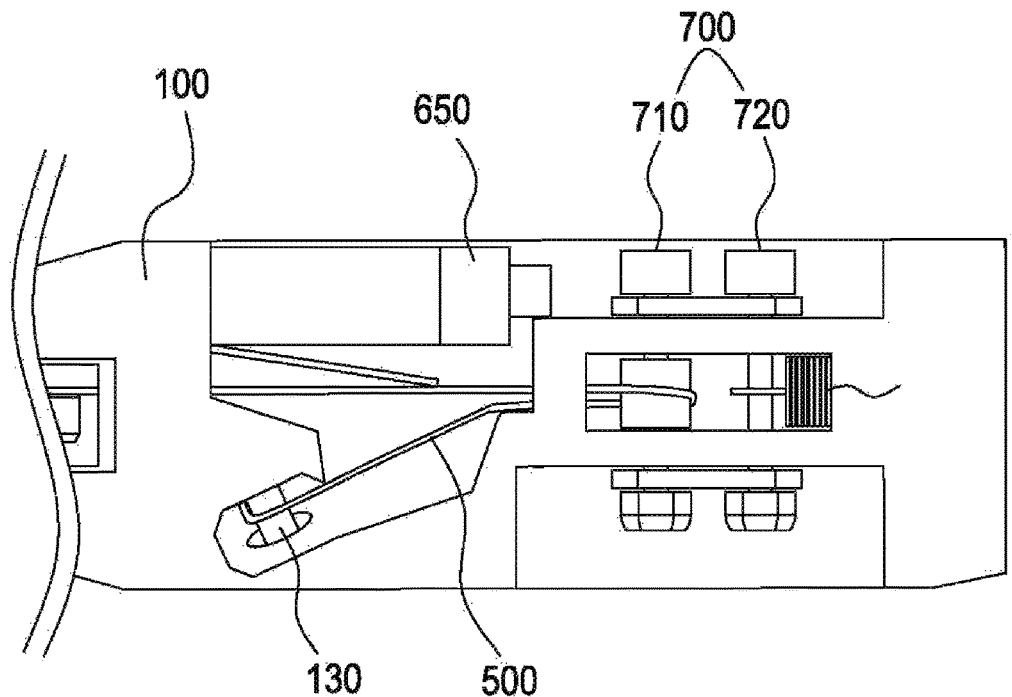
FIG. 12 is a view illustrating an operation of a second switch part of the electronic artificial hand according to the embodiment of the present invention.
Figure 12:
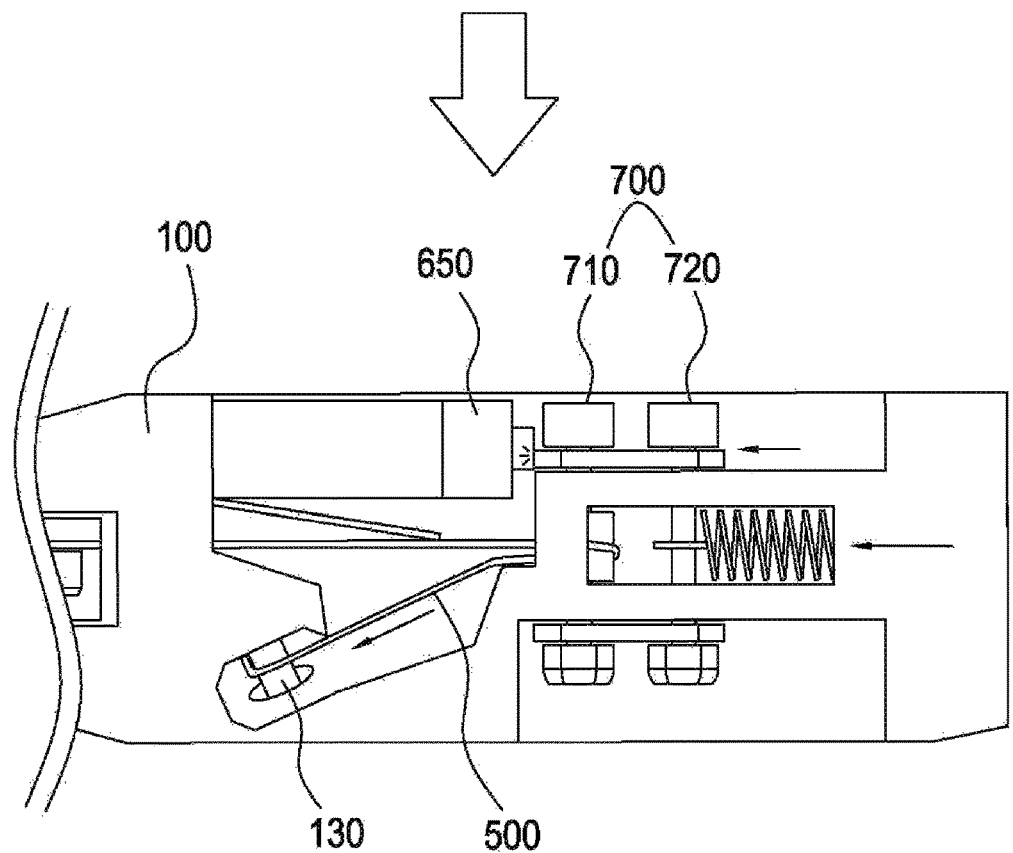

Referring to FIGS. 11 and 12, the body part 100 may stop the excessive joint movement of the finger groups 10 in the one direction (a), and may include a support member 700, a guide groove 750, a second switch part 650, and a spring section 760 capable of providing the predetermined gripping force to the finger groups 10.

The support member 700 allows the tendon section 500 to be hooked thereon and reverses a direction of movement of the tendon section 500. In detail, the support member 700 may be provided in a stick shape. The tendon section 500 has one end connected to the power section 400, and the other end passing through the tendon path 501 formed in the one end of the body part 100 to be connected to the first knuckle 210, and the tendon section 500 is provided to be hooked on the support member 700 and then connected to the support member 700 while passing from the power section 400 to the one end of the body part 100. Accordingly, the support member 700 may be provided as a cylindrical support member 700 to minimize damage of the tendon section 500. Further, the support member 700 may be engaged with the guide groove 750 to move along the guide groove 750. The guide groove 750 may be formed along a longitudinal direction of the body part 100. In detail, the guide groove 750 is formed in one end and the other end directions of the body part 100 to guide the support member 700. In more detail, the guide groove 750 is formed in the one end direction of the body part 100 in which the tension of the tendon section 500 is generated.

The support member 700 allows the tendon section 500 to be hooked thereon, in order to be capable of reversing the proceeding direction of the tendon section 500 and receiving the tension of the tendon section 500. Further, the support member 700 is engaged with the spring section 760 having a predetermined restoring force to provide the predetermined gripping force. Further, the support member 700 presses the second switch part 650. As described above, the support member 700 may make various actions and may include a first stick 710 on which the tendon section 500 is hooked, a second stick 720 on which the spring section 760 is hooked, and a connection member configured to connect the first stick 710 and the second stick 720 and press the second switch part 650, to be smoothly operated.

The second switch part 650 is provided to prevent the excessive joint movement of the finger groups 10 in the one direction (a). The second switch part 650 is provided on one end of the guide groove 750. The second switch part 650 is provided on one end of the guide groove 750 and pressed by the support member 700 configured to move along the guide groove 750.

The body part 100 may include the spring section 760 to apply the predetermined gripping force to the finger groups 10. The spring section 760 has one end engaged with the support member 700 and the other end engaged with the other end of the guide groove 750. In detail, since the spring section 760 has the one end engaged with the support member 700 and the other end engaged with the body part 100 at the other end of the guide groove 750, the support member 700 may stay at the other end of the guide groove 750. The spring section 760 has the predetermined restoring force. Specifically, the spring section 760 is provided to have a restoring force greater than the tension of the tendon section 500 generated when the finger groups 10 perform joint movement in the one direction (a) due to winding (a') of the tendon section 500 of the power section 400 and a restoring force relatively smaller than when the tension of the tendon section 500 becomes greater because the finger groups 10 grip the target object and no longer perform joint movement in the one direction (a). More specifically, when the finger groups 10 perform joint movement in the one direction (a) due to winding (a') of the tendon section 500 of the power section 400, grip the target object 4, and no longer perform joint movement, the tension of the tendon section 500 becomes greater due to winding (a') of the power section 400, and in this case, since the tension of the tendon section 500 becomes greater than the restoring force of the spring section 760, the support member 700 engaged with the spring section 760 is moved in the one direction (a) along the guide groove 750 by the tension of the tendon section 500 to press the second switch part 650. That is, in the spring section 760, the support member 700 on which the tendon section 500 is hooked is moved to the switch part along the guide groove 750 to press the second switch part 650 when the tension of the tendon section 500 generated by winding (a') of the power section 400 is greater than an elastic force of the spring section 760, and the second switch part 650 stops the power section 400 when being pressed by the support member 700.

An example is shown wherein the electronic artificial hand according to the embodiment of the present invention includes both the first switch part and the second switch part, but in another embodiment, only one of the first switch part and the second switch part may be used, and the above-described embodiment is also included in the present invention.

Figure 8:
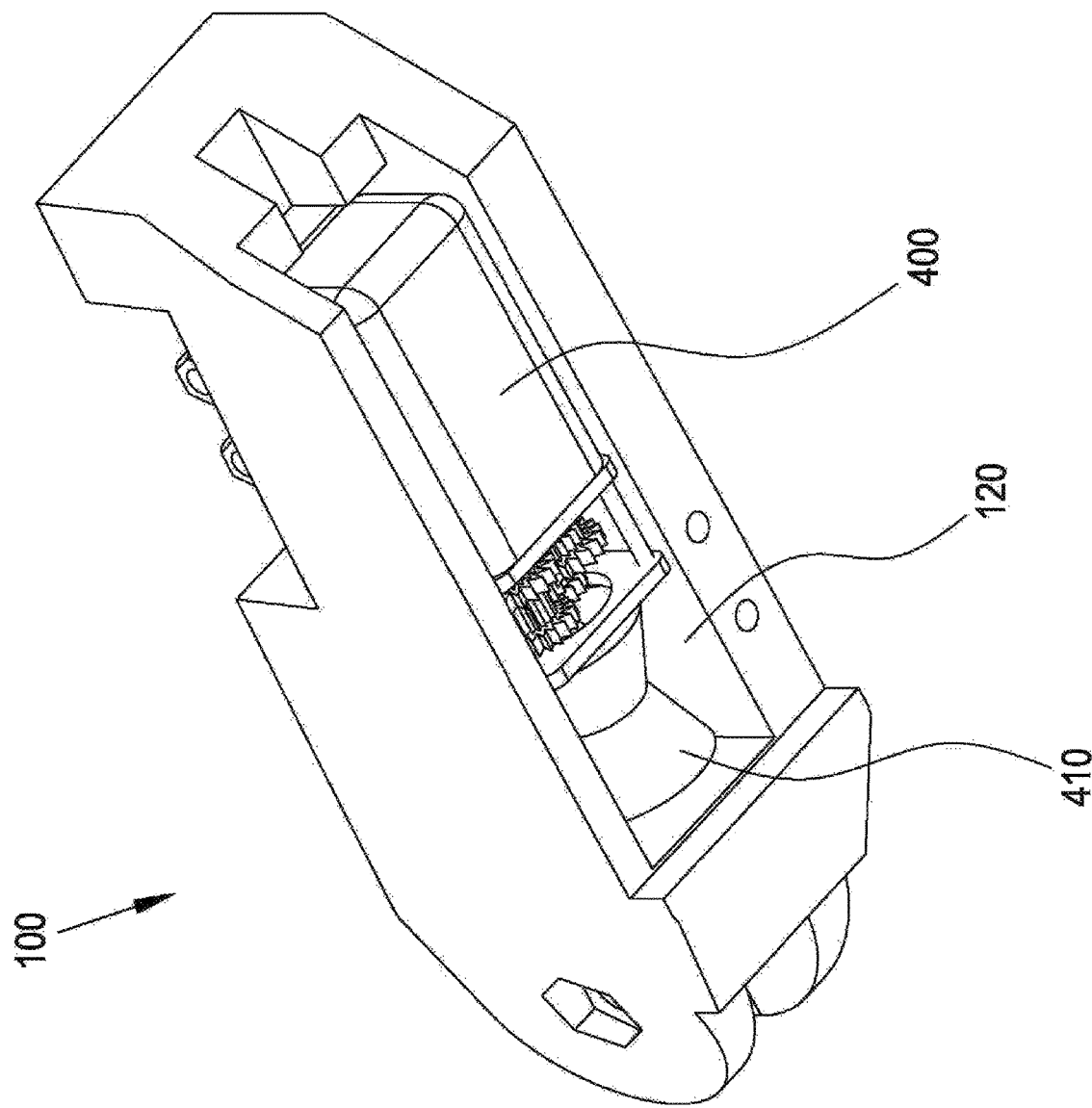
FIGS. 8 to 10 are views illustrating a body part of the electronic artificial hand according to the embodiment of the present invention.
Figure 9:
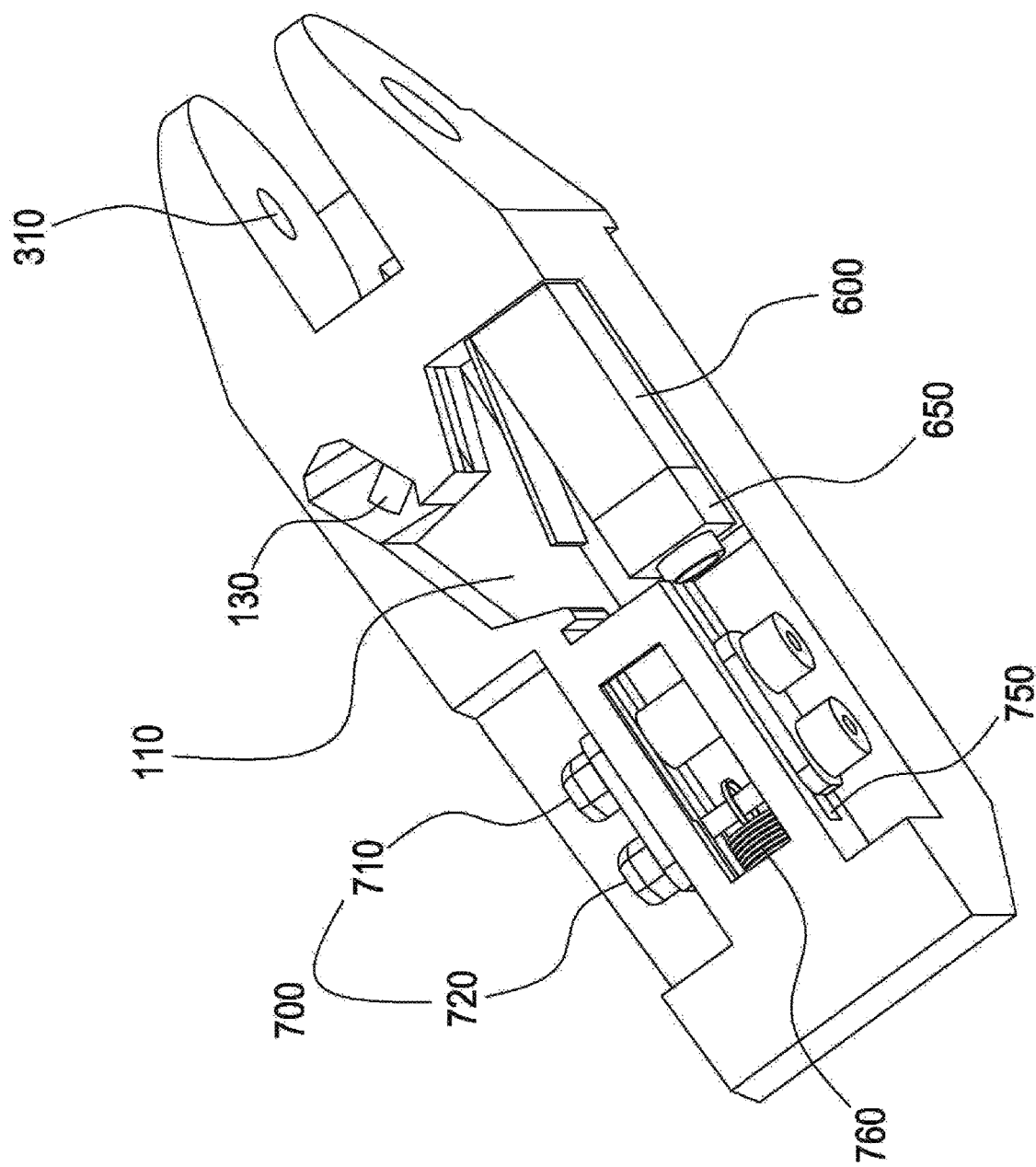
Figure 10:
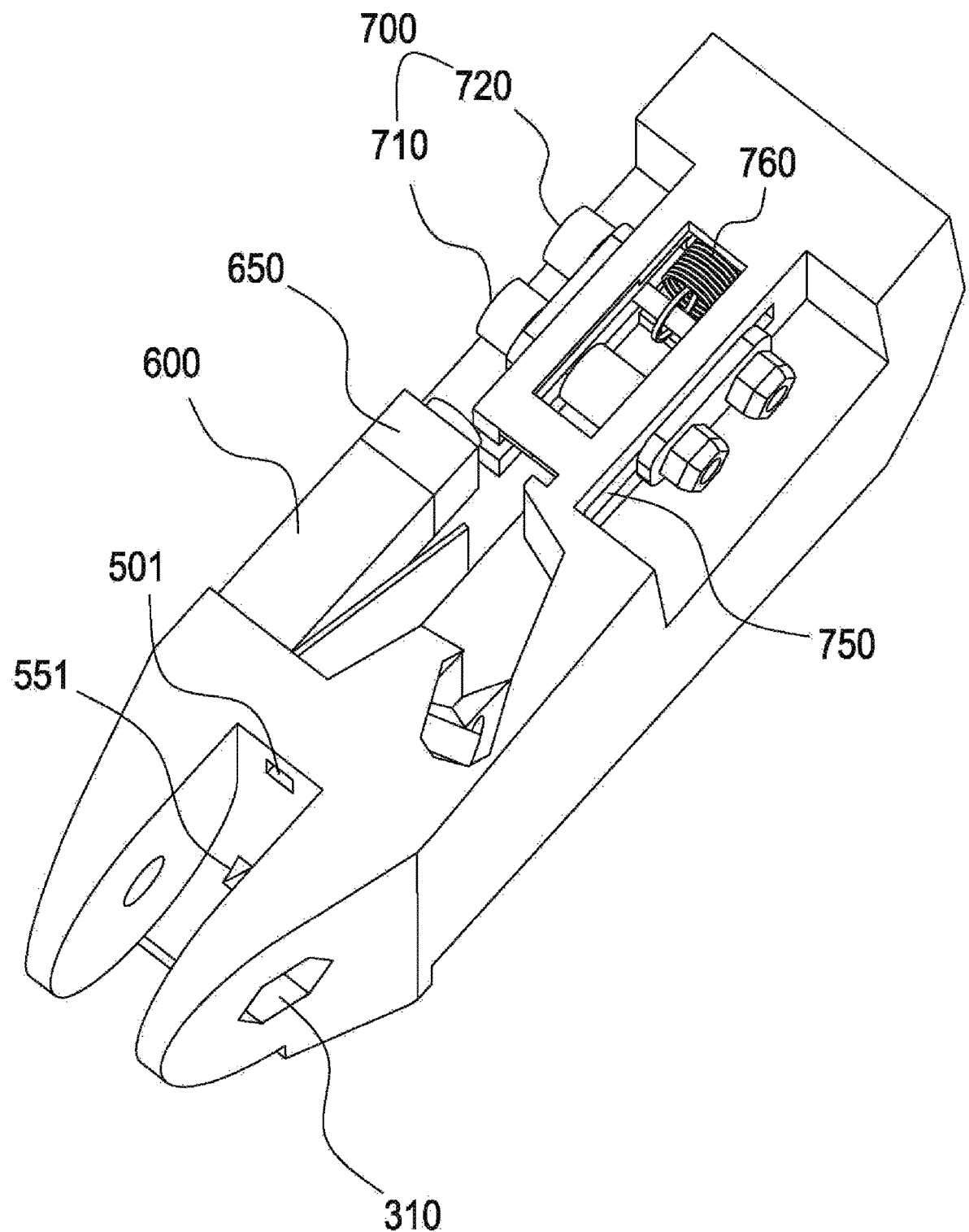

Referring to FIGS. 8 and 9, body part 100 may be partitioned to form two layers. In detail, the body part 100 may be partitioned into an upper layer 110 and a lower layer 120 so that a narrow space may be efficiently used. The body part 100 may include the power section 400 in the lower layer 120 and the switch part, the first switch part 600, or the second switch part 650 in the upper layer 110. The tendon section 500 connected to the power section 400 may be moved to the upper layer 110, and a roller part 130 may be further provided so that the moved tendon section 500 may face the support member 700.

Figure 16:
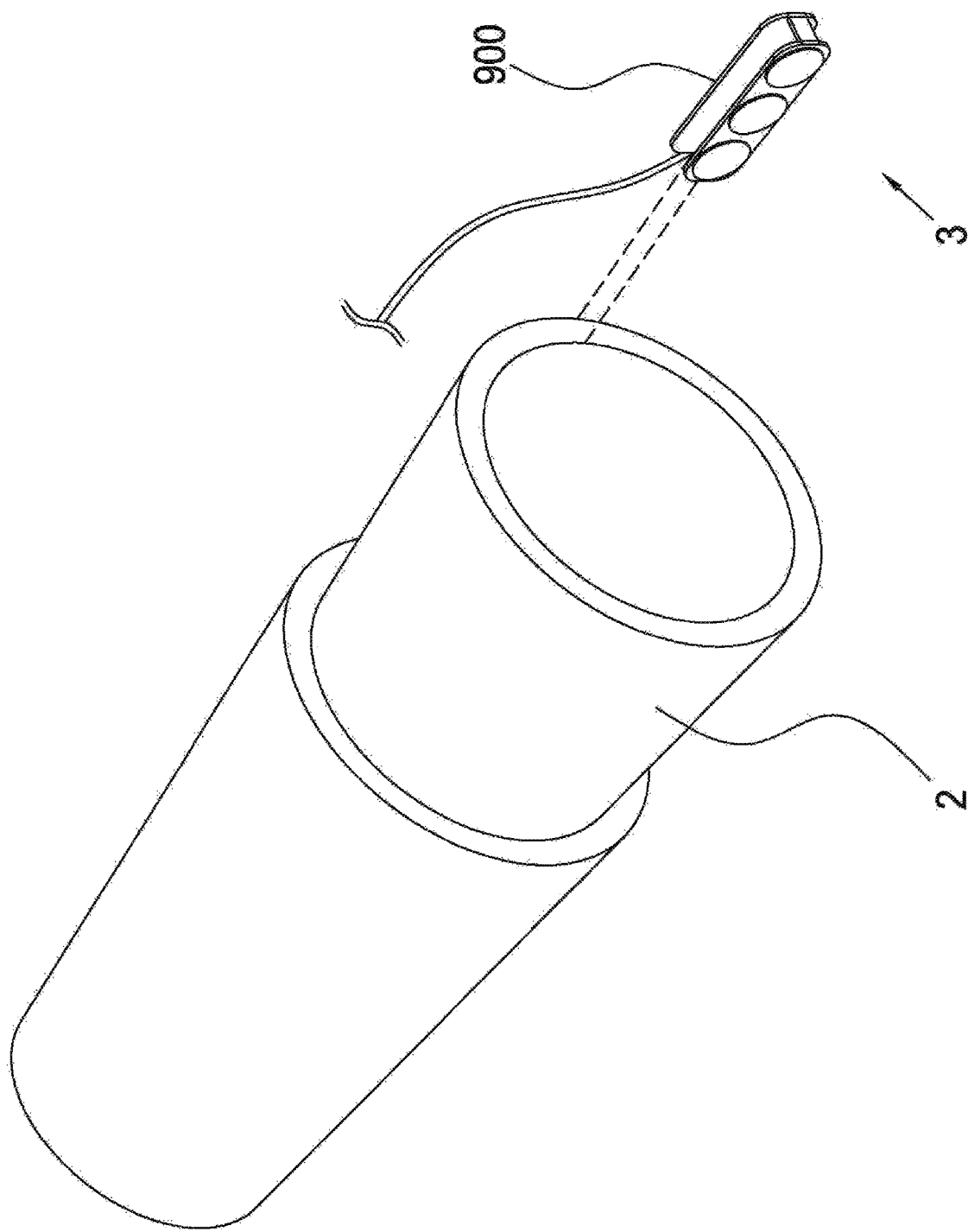
FIG. 16 is a view illustrating a controller of the electronic artificial hand according to the embodiment of the present invention.

Referring to FIG. 16, the controller 3 is a part configured to operate the power section 400 and operates the power section 400 according to an input of the user. In detail, the controller 3 may be electrically connected to the power section 400. The controller 3 may be an electromyogram sensor 900 configured to sense currents of muscles.

Figure 15:
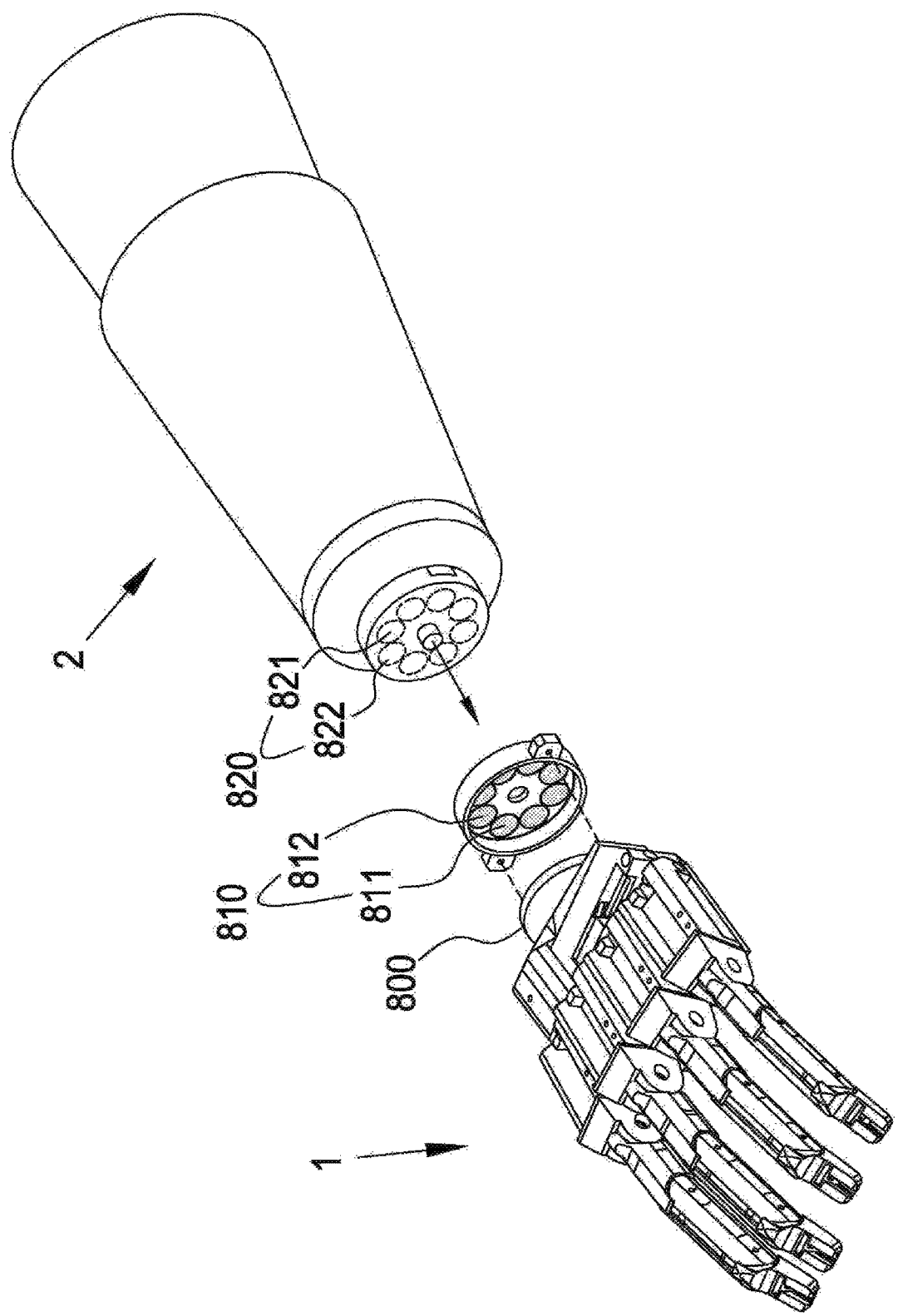
FIG. 15 is a view illustrating engagement relation between the gripping part and a wearing part of the electronic artificial hand according to the embodiment of the present invention.

Referring to FIGS. 1 and 15, the gripping part 1 may include a coupling part 800 configured to engage and fix the body part 100 of each of the five finger groups 10 and connect the gripping part 1 to the wearing part 2.

The wearing part 2 may be provided as a socket part worn on the impaired area. The socket part has a predetermined groove therein and is fitted onto the impaired area of a patient to be fixed. One end of the wearing part 2 is engaged with the gripping part 1.

The wearing part 2 and the coupling part 800 may be engaged with each other through a plurality of magnets or electromagnets. In detail, the one end of the wearing part 2 and the coupling part 800 may be engaged with each other through the magnets. In more detail, the wearing part 2 may be coupled to the coupling part 800 through a magnet part in which the S-pole and the N-pole are alternatively and sequentially arranged. The magnet part includes a first magnet part 810 formed on the wearing part 2, and a second magnet part 820 formed on the coupling part 800. Specifically, the first magnet part 810 and the second magnet part 820 are alternatively and sequentially arranged with the S-pole and the N-pole. More specifically, the S-pole and the N-pole are alternatively and sequentially arranged in the first magnet part 810 and the second magnet part 820 and may be circularly arranged. More specifically, a first S-pole 812 and a first N-pole 811 are alternatively arranged in the first magnet part 810, and a second S-pole 822 and a second N-pole 821 are alternatively arranged in the second magnet part 820. Since the S-pole and the N-pole are alternatively and sequentially arranged in the first magnet part 810 and the second magnet part 820, the first magnet part 810 and the second magnet part 820 may be engaged with each other at various angles.

Exemplary embodiments of the present invention are disclosed for exemplary purposes, and those skilled in the art may change, modify, and add without departing from the spirit and the scope of the present invention, and change, modification, and addition should be within the claims.

Since those skilled in the art may variously replace, transform, and modify the present invention without departing from the spirit of the present invention, the present invention is not limited by the above-described embodiments and the accompanying drawings.

REFERENCE NUMERALS

1: gripping part 2: wearing part
3: controller 4: target object
10: finger group 11: thumb group
12: index finger group 13: middle finger group
14: ring finger group 15: little finger group
100: body part 110: upper layer
120: lower layer 130: roller part
200: knuckle part 210: first knuckle
220: second knuckle 230: third knuckle
250: protrusion 300: joint part
310: first joint part 320: second joint part
330: third joint part 400: power part
410: winding part 500: tendon part
501: tendon path 550: restoring line part
551: restoring line path 600: first switch part
650: second switch part 700: support member
710: first stick 720: second stick
750: guide groove 760: spring part
800: coupling part 810: first magnet part
811: first N-pole 812: first S-pole
820: second magnet part 821: second N-pole
822: second S-pole 900: electromyogram sensor
a: one direction (a) a: winding
b: the other direction (b) b': unwinding

The invention claimed is:

1. An electronic artificial hand comprising:
a plurality of finger groups configured to perform a gripping operation through joint movement in one direction or perform unfolding movement through the joint movement in another direction,
wherein each of the plurality of finger groups includes:
a body part including a power section;
a plurality of knuckles sequentially engaged with each other, one of the plurality of knuckles being connected to one end of the body part;
a plurality of joints disposed between the plurality of knuckles to perform the joint movement in the one direction or in the another direction at a predetermined angle;
a tendon path (501) disposed in the respective knuckle to be eccentric in the one direction on the basis of the respective joint;
a restoring line path formed to be eccentric in the another direction;
a tendon section having one end configured to be connected to the power section to be wound and another end passing through the body part and the tendon path of the respective knuckle to be connected to the most distal one of the plurality of knuckles; and
a restoring line section having a restoring force and having one end connected to the body part and another end passing through the restoring line path of the respective knuckle to be connected to the most distal one of the plurality of knuckles,
wherein the body part further includes a first switch configured to stop the power section by using tension of the tendon section which is variable when the power section winds or unwinds the tendon section.

2. The electronic artificial hand of claim 1, wherein the body part includes the first switch at a location adjacent to the tendon section, and
wherein:
the first switch is configured to be pressed by the tension of the tendon section generated by the restoring force of the restoring line section and decompressed when the tension is removed because the power section is unwound; and
the unwinding of the power section is stopped when the first switch is decompressed.

3. The electronic artificial hand of claim 2, wherein the tendon section has a length greater than that of the tendon path, and the tension is removed due to the unwinding of the power section.

4. The electronic artificial hand of claim 2, wherein the first switch is a limit switch.

5. The electronic artificial hand of claim 1, wherein the body part includes:
- a support member, on which the tendon section is hooked, configured to reverse a proceeding direction of the tendon section;
- a guide groove, with which the support member is engaged, configured to guide the support member moved along a direction in which the tension of the tendon section is generated;
- a second switch provided in one end of the guide groove and configured to be pressed due to movement of the support member; and
- a spring section having one end connected to the support member and another end connected to another end of the guide groove, wherein:
the support member is configured to move to the first switch along the guide groove to press the second switch when the tension of the tendon section generated due to the winding of the power section is greater than a restoring force of the spring section; and
the winding of the power section is stopped when the second switch is pressed by the support member.

6. The electronic artificial hand of claim 1, wherein the body part includes the first switch at a location adjacent to the tendon section, and wherein:
the first switch is configured to be pressed by the tension of the tendon section generated by the restoring force of the restoring line section and decompressed when the tension is removed because the power section is unwound,
the unwinding of the power section is stopped when the first switch is decompressed;
the body part includes a support member, on which the tendon section is hooked, configured to reverse a proceeding direction of the tendon section, a guide groove, with which the support member is engaged, configured to guide the support member moved along a direction in which the tension of the tendon section is generated, a second switch provided in one end of the guide groove and pressed due to movement of the support member, and a spring section having one end connected to the support member and another end connected to another end of the guide groove;
the support member is configured to move to the first switch along the guide groove to press the second switch when the tension of the tendon section generated due to the winding of the power section is greater than a restoring force of the spring section; and
the winding of the power section is stopped when the second switch is pressed by the support member.

7. The electronic artificial hand of claim 1, wherein the body part has two layers, and wherein:
the power section is provided in one of the two layers; and
the switch part is provided in the other layer of the two layers.

8. The electronic artificial hand of claim 1, wherein the plurality of knuckles sequentially include a first knuckle, a second knuckle and a third knuckle.

9. The electronic artificial hand of claim 1, wherein:
the plurality of finger groups include five finger groups;
one of the plurality of finger groups is a thumb group; and
the thumb group is provided at an angle different from those of the remaining four finger groups, and an end of the thumb group is configured to comes come into contact with at least one respective end of the remaining four finger groups when the plurality of finger groups perform the joint movement in the one direction.

* * * * *